US006303568B1

United States Patent
Jaynes et al.

(10) Patent No.: US 6,303,568 B1
(45) Date of Patent: *Oct. 16, 2001

(54) THERAPEUTIC ANTIMICROBIAL POLYPEPTIDES, THEIR USE AND METHODS FOR PREPARATION

(75) Inventors: Jesse M. Jaynes; Frederick M. Enright; Kenneth L. White, all of Baton Rouge, LA (US)

(73) Assignee: Helix Biomedix, Inc., New Orleans, LA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/749,066

(22) Filed: Nov. 14, 1996

Related U.S. Application Data

(63) Continuation of application No. 08/575,058, filed on Dec. 21, 1995, now abandoned, which is a continuation of application No. 08/410,003, filed on Mar. 23, 1995, now abandoned, which is a continuation of application No. 08/168,908, filed on Dec. 16, 1993, now abandoned, which is a continuation of application No. 07/978,120, filed on Nov. 18, 1992, now abandoned, which is a continuation of application No. 07/831,082, filed on Feb. 5, 1992, now abandoned, which is a continuation of application No. 07/069,653, filed on Jul. 6, 1987, now abandoned.

(51) Int. Cl.$^7$ ............................. A61K 38/00; A01N 37/18
(52) U.S. Cl. ............................ 514/2; 530/310; 530/324; 530/326
(58) Field of Search .................... 530/310, 324, 530/326; 514/2

(56) References Cited

U.S. PATENT DOCUMENTS

| 3,911,110 | 10/1975 | Smirnoff . | |
|---|---|---|---|
| 4,355,104 | * 10/1982 | Hultmark et al. | 435/70 |
| 4,520,016 | * 5/1985 | Hultmark et al. | 514/12 |
| 4,579,821 | 4/1986 | Palmiter et al. . | |
| 4,643,988 | 2/1987 | Segrest et al. . | |
| 4,704,362 | 11/1987 | Itakura et al. . | |
| 4,844,924 | 7/1989 | Stanley . | |
| 4,962,028 | 10/1990 | Bedbrook et al. . | |
| 5,045,531 | * 9/1991 | Berkowitz | 574/12 |
| 5,206,154 | * 4/1993 | Lai et al. | 435/69.7 |

FOREIGN PATENT DOCUMENTS

| 0043075 | 6/1982 | (DE) . |
|---|---|---|
| 0157351 | 10/1985 | (DE) . |
| 0182278 | 5/1986 | (DE) . |
| WO88/00976 | 2/1988 | (EP) . |
| 063949 | 11/1982 | (GB) . |
| 117600 | 9/1984 | (GB) . |
| 0142924 | 5/1985 | (GB) . |
| 140556 | 5/1985 | (GB) . |
| 0184288 | 6/1986 | (GB) . |
| WO86/04356 | 7/1986 | (WO) . |

OTHER PUBLICATIONS

Meanfield et al. Biochemistry 21:5020–5031. 1982.*
Durtz et al in Basic & Clinical Immunology p 197–203 1984.*
Von Hofster et al Molecular Cloning, cDNA sequencing, etc . . . PNAS 82: 2240–2243 1985.*
Rennell et al Phage P22 Lysis genes . . . Virology 143:280–289. 1985.*
Nakajima et al. Interaction Between Leposons & Sarcotoxin IA JBC 262:1665–1669. 1987.*
Bessler et al Interaction of Membrane Modifying . . . BBRC 87:99–105. 1979.*
Anderson, Lucy, *J. Cell Sci.*, "Protein Synthesis and Uptake by Isolated Cecropia Oocytes", 1971, 8:735–750.
Andreu, D., et al. *Proc. Natl. Acad. Sci.*, "Solid–phase synthesis of Cecropin A and Related Peptides", 1983, 80:6475–6479.
Andreu, D., et al. *Biochemistry*, "N–Terminal Analogues of Cecropin A: Synthesis, Antibacterial Activity, and Conformational Properties", 1985, 24:1683–1688.
Bernheimer, A.W., et al. *Biochimica et Biophysica Acta*, "Interactions between Membranes and Cytolytic Peptides", 1986, 86:123–141.
Bessler, W.G., *Biochemical and Biophysical Research Communications*, "Interaction of Membrane Modifying Peptide Antibiotics from Trichodermaviride with Leukocytes", 1979, 87:99–105.
Blasi, Udo, *Gen. Virol.*, "Influence of C–terminal Modifications of ΦX174 Lysis Gene E on its Lysis–inducing Properties", 1985, 66:1209–1213.
Boman, H.G., *Developmental and Comparative Immunology*, "On the Primary Structures of Lysozyme, Cecropins and Attacins from *Hyalophora cecropia*", 1985, 9:551–558.
Boman, H.G., *Ann. Rev. Microbiol.*, "Cell–Free Immunity in Insects", 1987 41:103–26.
Buckley, K.J., *Mol. Gen. Genet*, "Lytic Activity Localized to Membrane–spanning Region of ΦX174 E Protein", 1986, 204:120–125.

(List continued on next page.)

Primary Examiner—Scott D. Priebe
Assistant Examiner—Anne Marie S. Beckerleg
(74) Attorney, Agent, or Firm—Baker Botts L.L.P.

(57) ABSTRACT

A novel class of antimicrobial agents for animal species including cecropins, attacins, lysozymes, phage derived polypeptides, such as those transcribed from gene 13 of phage 22, an S protein from lambda phage, and an E protein from phage PhiXl74, as well as, synthetically derived polypeptides of similar nature. The antimicrobial agents can be used to treat microbial infections and as components of medicinal compositions. The genes encoding for such antimicrobial agents can be used to transform animal cells, especially embryonic cells. The transformed animals including such antimicrobial cells are also included.

12 Claims, No Drawings

OTHER PUBLICATIONS

Coleman, Jack, *Cell*, "The use of RNAs Complementary to Specific mRNAs to Regulate the Expression of Individual Bacterial Genes", 1984, 37:429–436.

Doel, M.T., *Nucleic Acids Research*, "Expression in *E. coli* of Synthetic Repeating Polymeric Genes Coding for Poly-(L–aspartyl–L–phenylalanine)", 1980, 8:4575–4593.

Drummond, M., *Nature*, "Launching Genes Across Phylogentic Barriers", 1983, 303:198–199.

Drutz, D., *Basic & Clinical Immunology*, "Immunity & Infection", 1984, 197–201.

Eglitis, Martin A., *Science*, "Gene Expression in Mice After High Efficiency Retroviral–Mediated Gene Transfer", 1985, 230:1395–1398.

*Electroporation* —"Transfection of Mammalian Cells in Culture" 18–3:293–295.

Engstrom, A., *The EMBO Journal*, "Insect Immunity. The Primary Structure of the Antibacterial Protein Attacin F and its Relation to Two Native Attacins from *Hyalophora cecropia*", 1984, 2:2065–2070.

Engstrom, A., *The EMBO Journal*, "Amino Acid and cDNA Sequences of Lysozyme from *Hyalophora cecropia*", 1985, 4:2119–2122.

Fingl, Edward, *The Pharmacological Basis of Therapeutics*, "General Principles" Chapter 1, 1975. p. 1–2.

Fuchs, R.L., *Applied and Enviromental Microbiology*, "Cloning of a Serratia marcesces Gene Encoding Chitinase", 1986, 51:504–509.

Garcia, Lopez, *Biochem Genetics*, 106:190368d "Production of Lysozyme of *Streptococcus pneumonia* in *Escherichia coli* by Recombinant DNA Technology", 1986.

Garrett, Jinnie, *Mol. Gen. Genet.*, "Cell Lysis by Induction of Cloned Lambda Lysis Genes", 1981, 182:326–331.

Gelehrter, Thomas D., *Biochem. and Biophys. Res. Comm.*, Stimulation of Monovalent Ion Fluxes and DNA Synthesis in 3T3 Cells by Melittin and Vasopressin . . . , 1980, 97:716–724.

Gibson, Bradford W., *The Journal of Biological Chemistry*, "Novel Peptide Fragments Originating from $PGL^a$ and the Caerulein and Xenopsin Precursors from Xenopus laevis*", 1986, 261:5341–5349.

Gilboa, Eli, *BioTechniques*, "Transfer and Expression of Cloned Genes Using Retroviral Vectors", 1986, 4:504–512.

Giovannini, Maria G., *Biochem. J.*, "Biosynthesis and Degradation of Peptides Derived from Xenopus laevis Prohormones", 1987, 243:113–120.

Hoppe, Peter C., *Biology of Reproduction*, "Fertilization In Vitro and Development of Mouse Ova", 1973 8:420–426.

Horiuchi, I., *Chemical Abstracts*, "Aricine as a Bactericide and Fungicide", vol. 97, p. 290, abstract 97:87036r, 1982.

Horwitz, Marc, *Mammalian Hormones*, "Genetic Improvement of Chitinase Production by *Serratia marcescens*", 1985, 102:216038R.

Hultmark, D., *Eur. J. Biochem.*, "Insect Immunity. Purification and Properties of Three Inducible Bactericidal Proteins from Hemolymph of Immunized Pupae of *Hyalophora cecropia*", 1980, 106:7–16.

Hultmark, D. *Eur. J. Biochem.*, "Insect Immunity: Isolation and Structure of Cecropin D Four Minor Antibacterial Components from Cecropia Pupae", 1982, 127:207–217.

Hultmark, D., *The EMBO Journal*, "Insect Immunity. Attacins, a Family of Antibacterial Proteins from *Hyalophora cecropia*", 1983, 2:571–576.

Huszar, D., *Proc. Natl. Acad. Sci. USA*, "Insertion of a Bacterial Gene into the Mouse Germ Line Using an Infectious Retrovirus Vector", 1985, 82:8587–8591.

Jaynes, J.M., *Appl. Microbiol. Biotechnol*, "Construction and Expression of Synthetic DNA Fragments Coding for Polypeptides with Elevated Levels of Essential Amino Acids", 1985, 21:200–205.

Kangas, T., *Applied and Environmental Microbiology*, Expression of a Proline–Enriched Protein in *Escherichia coli*, 1982, 43:629–635.

Kockum, K., *The EMBO Journal*, "Insect Immunity. Isolation and Sequence of Two cDNA Clones Corresponding to Acidic and Basic Attacins from *Hyalophora cecropia*", 1984, 3:2071–2075.

Lee, J.Y., *The EMBO Journal*, "Insect Immunity. Isolation of cDNA Clones Corresponding to Attacins and Immune Protein P4 from *Hyalophora cecropia*" 1983, 2:577–581.

Matthias, P., *Chemical Abstracts*, "Transient Expression of the Chicken Lysozyme Gene after Transfer into Human Cells", 1983, 98:12350a.

Merrifield, R.B., *Biochemistry*, "Synthesis of the Antibacterial Peptide Cecropin A(1–33)", 1982, 21:5020–5031.

Nakai, T., *Chemical Abstracts*, "Synthesis of Self–defense Substance Produced by Silkworm, Lepidopteran, and Related Peptides", 1986, 106:214351w.

Nakajima, Y., *Biological Chemistry*, "Interaction Between Liposomes and Sarcotoxin IA, a Potent Antibacterial Protein of *Sarcophaga peregrina* (Flesh Fly)* ", 1987, 262:1665–1669.

Nicolson, G., *The Journal of Cell Biology*, "Ultrastructural Localization of Lectin–Binding Sites on the Zonae Pellucidae and Plasma Membranes of Mammalian Eggs", 1975, 66:263–274.

Okada, M., *Biochem. J.*, "Ionophore Activity of Sarcotoxin I, a Bactericidal Protein of *Sacrophaga peregrina*", 1985, 299:453–458.

Kemp J.D., *Chemical Abstracts*, "Transfer of a Functional Gene via the Ti Plasmid", vol. 101, No. 3, Jul. 1984, pp. 176–177.

Pownall, H. J., *Biochem. and Biophys. Res. Comm.*, "The Helical Hydrophobic Moment Avoids Prolines in Phosholipid–binding Proteins", 1986, 139:202–208.

Rennell, D., *Virology*, "Phage P22 Lysis Genes: Nucleotide Sequences and Functional Relationships with T4 and v Genes", 1985, 143:280–289.

Sawazaki, I. *Chemical Abstracts*, "Enzymic fungicides", vol. 87, p. 160, abstract 87:79669c.

Shiba, T., *Chemical Abstracts*, "Antimicrobial Peptides from Silkworm Hemolymph", 104:230430k.

Shih, D., *Proc. Natl. Acad. Sci. USA*, "Cell–free Synthesis and Processing of the Proteins of Poliovirus", 1978, 75:5807–5811.

Shih, D., *Journal of Virology*, "Translation of Encephalomyocarditis Virus RNA in Retriculocyte Lysates: Kinetic Analysis of the Formation of Viron Proteins and a Protein Required for Processing", 1979, 30:472–480.

Soto–Gil, R., "Cloning of Vibrio harveyi Chitinase and Chitoblast Genes in *Escherichia coli*, " 1984, 209–223.

Steiner, H., *Nature*, "Sequence and Specificity of two Antibacterial Proteins Involved in Insect Immunity", 1981, 292:246–248.

Van der Putten, H., *Proc. Natl. Acad. Sci.*, "Efficient Insertion of Genes into the Mouse Germ Line via Retroviral Vectors", 1985, 82:6148–6152.

Van Hofsten, P., *Proc. Natl. Acad. Sci. USA*, "Molecular Cloning, cDNA Sequencing, and Chemical Synthesis of Cecropin B from Hyalophora cecropia", 1985, 82:2240–2243.

Werneke, J.M., *Gene*, "Development of Broad–Host–Range Vectors for Expression of Cloned Genes in *Pseudomonas*", 1985, 38:73–84.

Wigler, M., *Cell*, "Transfer of Purified Herpes Virus Thymidine Kinase to Cultured Mouse Cells", 1977, 11:223–232.

*Central Patents Index*, Basic Abstracts Journal, Section C, AGDOC, Jul.

Partial Search Report for European Patent Application EP 88 90 6595.9 Jun. 27, 1991.

Patent Cooperation Treaty International Search Report for Application No. PCT/US88/02272, Nov. 15, 1988.

Partial Search Report for European Application No. EP 90 90 6453.7 Jun. 19, 1992.

Patent Cooperation Treaty International Search Report for Application No. PCT/US90/01945, Jul. 30, 1990.

Supplementary Search Report for European Patent Application No. EP 88 90 6511.6, Jan. 18, 1991.

* cited by examiner

SEQUENCE LISTING

<160> NUMBER OF SEQ ID NOS: 13

<210> SEQ ID NO 1
<211> LENGTH: 37
<212> TYPE: PRT
<213> ORGANISM: Hyalophora cecropia
<220> FEATURE:
<221> NAME/KEY: MOD_RES
<222> LOCATION: (37)..(37)
<223> OTHER INFORMATION: AMIDATION

<400> SEQUENCE: 1

Met Pro Lys Trp Lys Val Phe Lys Lys Ile Glu Lys Val Gly Arg Asn
1               5                   10                  15

Ile Arg Asn Gly Ile Val Lys Ala Gly Pro Ala Ile Ala Val Leu Gly
                20                  25                  30

Glu Ala Lys Ala Leu
            35

<210> SEQ ID NO 2
<211> LENGTH: 35
<212> TYPE: PRT
<213> ORGANISM: Hyalophora cecropia
<220> FEATURE:
<221> NAME/KEY: MOD_RES
<222> LOCATION: (35)..(35)
<223> OTHER INFORMATION: AMIDATION

<400> SEQUENCE: 2

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
                20                  25                  30

Lys Ala Leu
        35

<210> SEQ ID NO 3
<211> LENGTH: 37
<212> TYPE: PRT
<213> ORGANISM: Hyalophora cecropia
<220> FEATURE:
<221> NAME/KEY: MOD_RES
<222> LOCATION: (37)..(37)
<223> OTHER INFORMATION: AMIDATION

<400> SEQUENCE: 3

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Lys
            35

<210> SEQ ID NO 4
<211> LENGTH: 35
<212> TYPE: PRT
<213> ORGANISM: Bacteriophage phi-X174

<400> SEQUENCE: 4

Met Val Arg Trp Thr Leu Trp Asp Thr Leu Ala Phe Leu Leu Leu Leu
1               5                   10                  15

Ser Leu Leu Leu Pro Ser Leu Leu Ile Met Phe Ile Pro Ser Phe Lys

```
            20                  25                  30

Arg Pro Val
        35

<210> SEQ ID NO 5
<211> LENGTH: 36
<212> TYPE: PRT
<213> ORGANISM: Bacteriophage P22

<400> SEQUENCE: 5

Met Lys Lys Met Pro Glu Lys His Asp Leu Leu Thr Ala Met Met Ala
1               5                  10                  15

Ala Lys Glu Gln Gly Ile Gly Ala Ile Leu Ile Phe Ala Met Ala Tyr
            20                  25                  30

Leu Arg Gly Arg
        35

<210> SEQ ID NO 6
<211> LENGTH: 35
<212> TYPE: PRT
<213> ORGANISM: Bacteriophage lambda

<400> SEQUENCE: 6

Met Lys Met Pro Glu Lys His Asp Leu Leu Ala Ala Ile Leu Ala Ala
1               5                  10                  15

Lys Glu Gln Gly Ile Gly Ala Ile Leu Ala Phe Ala Met Ala Tyr Leu
            20                  25                  30

Arg Gly Arg
        35

<210> SEQ ID NO 7
<211> LENGTH: 26
<212> TYPE: PRT
<213> ORGANISM: Apis mellifera

<400> SEQUENCE: 7

Gly Ile Gly Ala Val Leu Lys Val Leu Thr Thr Gly Leu Pro Ala Leu
1               5                  10                  15

Ile Ser Trp Ile Lys Arg Lys Arg Gln Gln
            20                  25

<210> SEQ ID NO 8
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 8
gatctatgcc gaaatggaaa gtcttcaaga aaattgaaaa agtcggtcgc aacattcgaa      60
acggtattgt caaggctgga ccagcgatcg cggttttagg cgaagccaaa gcgctaggat     120
aa                                                                    122

<210> SEQ ID NO 9
<211> LENGTH: 123
<212> TYPE: DNA
<213> ORGANISM: Artificial Sequence
<220> FEATURE:
<223> OTHER INFORMATION: Synthetic Sequence
<400> SEQUENCE: 9
aattcttatc ctagcgcttt ggcttcgcct aaaaccgcga tcgctggtcc agccttgaca      60
```

```
ataccgtttc gaatgttgcg accgactttt tcaattttct tgaagacttt ccatttcggc    120
ata                                                                  123

<210> SEQ ID NO 10
<211> LENGTH: 81
<212> TYPE: DNA
<213> ORGANISM: Artificial Sequence
<220> FEATURE:
<223> OTHER INFORMATION: Synthetic Sequence

<400> SEQUENCE: 10
gatctatgaa cttctcccgt atcttttct tcgttttcgc tctggttctg gcttctactg     60
tttccgctgc accggaaccg g                                              81

<210> SEQ ID NO 11
<211> LENGTH: 81
<212> TYPE: DNA
<213> ORGANISM: Artificial Sequence
<220> FEATURE:
<223> OTHER INFORMATION: Synthetic Sequence

<400> SEQUENCE: 11
gatcccgggt ccggtgcagc ggaaacagta gaagccagaa ccagagcgaa aacgaagaaa    60
aagatacggg agaagttcat a                                              81

<210> SEQ ID NO 12
<211> LENGTH: 81
<212> TYPE: DNA
<213> ORGANISM: Artificial Sequence
<220> FEATURE:
<223> OTHER INFORMATION: Synthetic Sequence

<400> SEQUENCE: 12
gatctatgag catccagcac ttccgtgttg ctctgccgtt ctttgctgct ttctgcctgc    60
cgggttttcg ctcacccgga g                                              81

<210> SEQ ID NO 13
<211> LENGTH: 81
<212> TYPE: DNA
<213> ORGANISM: Artificial Sequence
<220> FEATURE:
<223> OTHER INFORMATION: Synthetic Sequence

<400> SEQUENCE: 13
gatcctccgg gtgagcgaaa acccggcagg cagaaagcag caaagaacgg cagagcaaca    60
cggaagtgct ggatgctcat a                                              81
```

THERAPEUTIC ANTIMICROBIAL POLYPEPTIDES, THEIR USE AND METHODS FOR PREPARATION

This application is a continuation of application Ser. No. 08/575,058, filed on Dec. 21, 1995, now abandoned; which is a continuation of application Ser. No. 08/410,003, filed on Mar. 23, 1995, now abandoned; which is a continuation of application Ser. No. 08/168,908, filed on Dec. 16, 1993, now abandoned; which is a continuation of application Ser. No. 07/978,120, filed on Nov. 18, 1992, now abandoned; which is a continuation of application Ser. No. 07/831,082, filed on Feb. 5, 1992, now abandoned; which is a continuation of application Ser. No. 07/069,653, filed on Jul. 6, 1987, now abandoned.

BACKGROUND OF THE INVENTION

This invention relates to certain therapeutic polypeptides useful in man and animals. Specifically, the therapeutic polypeptides are useful in cases of intra- and extracellular bacteria, fungi and protozoa which are either resistant to conventional antibiotics, difficult to treat without harm to the host cells, associated with severe infections, or connected with cases of traumatized or immune compromised hosts. In view of the properties of the therapeutic polypeptides of this invention which include definite antibacterial, anti-fungal and anti-protozoan activity, the therapeutic polypeptides provided herein are termed antimicrobial polypeptides.

Further, this invention relates to biosynthetic processes affording the antimicrobial polypeptides, including cloning or producing the desired polypeptides in various media, both as active antimicrobial polypeptides and also in the pro-form or the inactive antimicrobial polypeptide form with subsequent activation procedures. Included in these processes and procedures for biosynthesis of the antimicrobial polypeptides of this invention are novel forms of the polypeptides themselves, synthetic or semi-synthetic polypeptides and cells, containing such novel polypeptides which are themselves novel compositions, or cell lines, or hybridoma.

Still further, this invention relates to novel cells, including animal cells, and particularly mammalian cells, containing such antimicrobial polypeptides, including various specific mammalian cell types which contain the antimicrobial polypeptides. Methods for treating mammals infected with certain bacteria, protozoa, or fungi, and which are resistant to known antibiotics or which are difficult to treat with such antibiotics are also included in the present invention. As a novel composition, the present invention includes specifically mammalian cells having genes encoding for such antimicrobial polypeptides; particularly, various specific embryonic cells having the genes encoding for the antimicrobial polypeptides are included in the present invention. Additionally, processes for and methods of preparing mammalian cells including the genes encoding for antimicrobial polypeptides of this invention using recombinant DNA techniques are a part of the present invention.

A number of the antimicrobial polypeptides have been found to be useful when the genes encoding therefor are incorporated into various plant species. Particularly, when introduced into the plant genome by means of Agrobacterium, the antimicrobial polypeptide encoding genes produce plant species much more resistant to certain bacterially induced disease conditions and plant pathogens. Such antimicrobial polypeptides and the incorporation of the genes encoding therefor are more fully described in U.S. patent application Ser. No. 889,225, filed Jul. 25, 1986, to Jaynes et al, which is incorporated herein by reference as if fully set forth.

Although antimicrobial polypeptides of the type envisioned in the present invention are known from the humoral response to bacterial infection of the *Hyalophora cecropia* (a species of large silk moth), prior to the discovery of Jaynes et al, supra, it was unknown that such antimicrobial polypeptides were useful against plant pathogens or how the same could be transformed into plants. It is likewise previously unknown before the present invention, that the antimicrobial polypeptides would be similarly effective in animal, and particularly mammalian species, against certain microorganisms, or what method could be employed to transform cells of such species therewith.

It is known that certain polynucleotide molecules can be expressible in a given host and have the sequence araB promoter operably linked to a gene which is heterologous to such host. The heterologous gene codes for a biologically active polypeptide. A genetic construct of a first genetic sequence coding for cecropin operably linked to a second genetic sequence coding for a polypeptide which is capable of supressing the biological effect of the resulting fusion protein towards an otherwise cecropin-sensitive bacterium, International Patent Publication WO86/04356, Jul. 31, 1986.

It is therefore an object of the present invention to provide antimicrobial polypeptides for therapeutic treatment of pathogens in mammals including bacteria, fungi, and protozoa. A further object is to provide a method for treatment of man and animals having a bacterial infection with an antimicrobial polypeptide for such infection. A still further object of the present invention is to provide for a biosynthetic process to produce such antimicrobial polypeptides. Another object of the present invention is to provide for novel synthetic and semisynthetic antimicrobial polypeptides produced by recombinant DNA procedures. A still further object of the invention provides cells from a host animal transformed by genetic sequences incorporated into the cells, and ultimately to provide transformed animals which are as a result resistant to a number of pathogenic microorganisms.

These and still other objects of the invention are provided according to the present invention as described in the following specification.

THE INVENTION

The present invention provides for a method for treatment of an animal having a bacterial infection caused by either or both gram-positive or gram-negative bacteria, such as by a member of the group consisting of Brucella, Listeria, Pseudomonas (other than *P. solanacium*), Staphylococcus or a protozoan infection caused by a member of the group consisting of Trypanosoma and Plasmodia, which method comprises administration to said mammal of an antibacterial amount of an antimicrobial polypeptide selected from the group consisting of a cecropin, an attacin, a lysozyme, a polypeptide transcribed from gene 13 of phage P22, an S protein from lambda phage, and an E protein from phage PhiX174. As another aspect of the present invention, there is provided a biosynthetic method for producing the antimicrobial polypeptides of the present invention which method includes the steps of (a) microinjecting a phosphate buffered solution of genes encoding for and an antimicrobial polypeptide into selected cells, and (b) culturing the cells to produce such antimicrobial polypeptide included in the genome of said cells.

In a still further aspect, precursor polypeptides for the antimicrobial polypeptides of the present invention are produced by a process which comprises the steps of:

(a) augmenting at the 5' end in the correct reading frame the genes encoding for the beta-lactamase gene of *E. coli* by fusing thereto genes encoding for at least one antimicrobial polypeptide free from internal methionine codons and having a methionine codon at the 5' end of the antimicrobial gene to produce an augmented *E. coli*;

(b) culturing the augmented *E. coli* under conditions to produce beta-lactamase modified by containing at least one said antimicrobial polypeptide;

(c) isolating the modified beta-lactamase;

internal methionine, and in the last 5 amino acids on the carboxy end. A semisynthetic cecropin having two additional amino acids, which are methionine and proline, added to the amino end of cecropin B and free from internal methionine, that is, preferably substituted with valine for the internal methionine of natural cecropin B, has shown good antimicrobial activity. The amino acid sequence for the cecropins and selected examples of other antimicrobial polypeptides of the present invention is shown in Table 1.

TABLE 1

(SEQ ID NO:1)
CECROPIN C-37     MetProLysTrpLysValPheLysLysIleGluLysValGlyArgAsnIleArgAsnGlyIleValLysAlaGlyProAlaIleAlaValLeuGly
                  GluAlaLysAlaLeuCONH₂

(SEQ ID NO:2)
NATURAL CECROPIN B   LysTrpLysValPheLysLysIleGluLysMetGlyArgAsnIleArgAsnGlyIleValLysAlaGlyProAlaIleAlaValLeuGlyGluAla
                     LysAlaLeuCONH₂

(SEQ ID NO:3)
NATURAL CECROPIN A   LysTrpLysLeuPheLysLysIleGluLysValGlyGlnAsnIleArgAspGlyIleIleLysAlaGlyProAlaValAlaValValGlyGlnAla
                     ThrGlnIleAlaLysCONH₂

(SEQ ID NO:4)
PhiX174 E PROTEIN-35   MetValArgTrpThrLeuTrpAspThrLeuAlaPheLeuLeuLeuLeuSerLeuLeuLeuProSerLeuLeuIleMetPheIleProSerPheLys
                       ArgProval (SEQ ID NO:5)
P22 P13--36   MetLysLysMetProGluLysHisAspLeuLeuThrAlaMetMetAlaAlaLysGluGlnGlyIleGlyAlaIleLeuIlePheAlaMetAlaTyr
              LeuArgGlyArg (SEQ ID NO:6)
LAMBDA PHAGE PROTEIN S   MetLysMetProGluLysHisAspLeuLeuAlaAlaIleLeuAlaAlaLysGluGlnGlyIleGlyAlaIleLeuAlaPheAlaMetAlaTyrLeu
                         ArgGlyArg (SEQ ID NO:7)
MELLITIN   GlyIleGlyAlaValLeuLysValLeuThrThrGlyLeuProAlaLeuIleSerTrpIleLysArgLysArgGlnGln (d) treating the modified beta-lactamase with cyanogen bromide to cleave the antimicrobial polypeptide; and (e) separating the antimicrobial polypeptide from the beta-lactamase, whereby an active antimicrobial polypeptide is formed.

The antimicrobial polypeptides of the present invention are relatively small having from about 30 to about 40 amino acids and, generally, as produced in natural settings include longer chains of amino acids, for example, of up to about 160 units in length. However, it is believed that the active portion of the naturally produced material selected for antimicrobial activity is between about 30 and about 40 amino acid units in length. Such a length is unusually small to have a widespread effect as an antimicrobial polypeptide. However, the in vitro tests, discussed below, have shown such antimicrobial activity to be present. Antimicrobial effects in insects have been noted for certain of the antimicrobial polypeptides. Specifically, the cecropins, attacins, and lysozymes were determined to be present in the humoral response to bacterial infection of the *Hyalophora cecropia*, as noted, supra, in the application of Jaynes et al. Cecropins, which are one example of a class of an antimicrobial polypeptide of the present invention include natural cecropin B, which has 35 amino acids, natural cecropin A which has 37 amino acids and differs from cecropin B by substituting leucine for valine or vice versa in 4 occurrences, for an Also shown in Table 1 is an antimicrobial polypeptide showing the first 35 amino acids transcribed from gene 13 of the phage P22. This phage is described in Rennell et al, Virology, 143, 280–289 (1985). A sample of the bacterium described therein was obtained from the author for use in this invention and propagated according to the directions provided. This reference is incorporated herein by reference as if fully set forth.

The S protein from Lambda phage is similar to that from phage P22, but has one less lysine unit at the amino end. A computer database search in Genbank was used to provide the DNA sequence for the S protein and the polypeptide sequence was derived by computer using DNA Inspector II.

Although smaller in amino acid chain length than the cecropins, the effective antimicrobial activity of the first 30 amino acid units of the E protein from phage PhiX174 is similar in scope. The E protein from phage PhiX174 is described by Buckley et al, Molecular General Genetics, Vol. 204, 120–125 (1986), which is incorporated herein by reference as if fully set forth.

The above described polypeptides have utility as therapeutic agents or antimicrobials for a wide variety of disease states and microbial conditions, including bacterial infections, certain fungal infections and some protozoal infections investigated. Of considerable interest are disease states which have long resisted treatment efforts, which are particularly serious, which result from both intracellular and extracellular organisms causing chronic debilitating etiologies, or which are associated with traumatized or immune compromised hosts. Specific bacterial examples are *Brucella abortus, Listeria monocytogenes, Pseudonomas aerugenosa*, and *Staphylococcus aureus*.

The in vitro effectiveness of the antimicrobial polypeptides is shown by simple exposure tests which provide a crude, but accurate, indication of activity. In general, such tests are carried out by exposing a known number of viable bacteria or other microorganism to one or more of the antimicrobial polypeptides of the present invention for a given time period. Following such treatment, the diluted or undiluted bacteria or microorganisms are inoculated on solid growth media or into an appropriate culture system and incubated. The microorganisms are then enumerated by the appropriate technique and the resulting numbers compared.

Several specific examples of in vitro tests were run on *E. coli* and *B. abortus* using the following general procedure:

Known numbers of bacteria are exposed to a known concentration of a selected antimicrobial agent of this invention. This mixture and appropriate controls were incubated at 37° C. for up to one hour. Following incubation, the mixtures are serially diluted and plated on an agar based growth media. The inoculated plates are incubated for 3 to 5 days at 37° C., after which the numbers of bacterial colonies are counted with the results expressed as the numbers of organisms per milliliter of the original mixture. The treated and control samples are then compared and expressed as absolute numbers of organisms or the log reductions of organisms.

A still further aspect of the present invention includes; animal cells containing antimicrobial polypeptides selected from a cecropin, an attacin, a lysozyme, a polypeptide transcribed from gene 13 of phage P22, an S protein from lambda phage and an E protein from the phage PhiX174. An additional aspect of the present invention is a process for producing animal cells containing such antimicrobial polypeptides which comprises transforming embryonic animal cells with genes encoding for such antimicrobial polypeptides using microinjection of pronuclear stage embryos. Another aspect of such a process for transformation of embryonic animal cells with genes encoding for such antimicrobial polypeptides includes transfection of early preimplantation stage embryos with retroviral vectors. Still another aspect of the present invention includes a process for producing animal cells which comprises transforming embryonic animal cells with genes encoding for such antimicrobial polypeptides using electroporation. Following each of these in vitro procedures, the transformed cells are reintroduced into the host or parent mammal for development and subsequent delivery, culturing or incubating the transformed eggs of aquatic species or fowl and hatching, as a transformed species, strain or breed having microbial resistance.

The transformation of animal cells employs cells of various types and can be used without difficulty in any cell type. Specifically, both differentiated and undifferentiated cells can be used as a cellular substrate for transformation. Typically, fibroblast cells, macrophage cells, primary cells, pluripotent embryonic stem cells, pluripotent hematopoietic stem cells, phagocytic cells, plasma cells, mast cells and carcinoma cells are useful cellular materials which can be successfully transformed to express the antimicrobial agents of this invention. The cells, once transformed by procedures described below, are then reintroduced into the host for antimicrobial activity.

According to this invention, the cells are transformed to contain one or more genes coding for polypeptide antimicrobial agents. The antimicrobial agents as contemplated by the present invention include insect-, phage-derived, and synthetic antimicrobial agents. Such insect-derived antimicrobial agents are known for their activity in combating diseases in certain insects caused by bacteria. The humoral response of such insects includes the production of attacins, lysozymes and cecropins as naturally expressed antimicrobial agents. The selection and application of such agents to animals and the transformation of animal cells to include genes coding for such antimicrobial agents into their genomes provides a hitherto unavailable possibility. In general, the antimicrobial agents are selected from attacins, lysozymes and cecropins. Further, phage-derived proteins have also been found to contain antimicrobial activity. Typical of such phage-derived antimicrobial agents include proteins and protein fragments containing lytic activity, such as an S protein from lambda phage, an E protein from phage PhiX174, and a protein from gene 13 of phage 22.

Cecropin polypeptides or proteins include several forms of which Cecropin A, Cecropin B, Cecropin D and a modified Cecropin B having 37 amino acids instead of the usual 35, as described supra, are preferred embodiments of antimicrobial agents with which to transform animal cells. In more preferred embodiments of the present invention, animal cell transformation is carried out by a process of treating discrete colonies of such cells or cell lines by treatment with selected chemical transformants, by treatment with a selected modified retrovirus vector, or by treatment employing electroporation.

Chemical transformation is a conventional procedure described by Wigler, M. et al, Cell 11:223–232 (1977), which is also known as DNA transfection in which the foreign gene or DNA is introduced into cells in culture as a part of a coprecipitate with calcium phosphate or dextran sulfate. The successful result of such procedure provides a viable cell containing one to many copies of the new gene which continuously expresses the new genetic information. Although less efficient than newer techniques, only one in a thousand (and typically one in a million) cells incorporate the new gene, DNA transfection provides a means for insertion of the antimicrobial agents of the present invention in the situation where the cell quantity is not limited.

Insertion of foreign DNA into cells by modified retrovirus vectors is a more recent development. As described by Gilboa et al, BioTechniques, Vol. 4, No. 6 (1986), pages 504–511, the technique provides for transferring a desired gene to a large fraction of a given cell population and is also referred to as retroviral-mediated gene transfer. Retroviruses have their viral genes encoded in RNA rather than DNA. When a virus penetrates a cell, the viral RNA is first converted to DNA, the DNA enters the nucleus and integrates randomly into a chromosome. The viral genes are expressed from the integrated provirus and progeny viruses are formed and leave by budding from the cell membrane. The antimicrobial agent genes of this invention are inserted into the retrovirus replacing the viral genes and using the viral integration process. A number of retrovirus vectors are useful in such a process, as described in Gilboa et al, supra, Typical are the retrovirus vectors identified as and selected from N2, N4, SAX, Mo+Py and M-MuLV. The foregoing is only an illustrative list which is non-limiting. Additional retroviral vectors will be identified and considered useful, as understood by skilled practitioners.

The technique of electroporation, while known and used primarily in plant cell work, has also been applied to animal cells recently. The electroporation process depends on the discovery that in culture medium containing DNA fragments or genes desired for insertion, the application of an electric field causes the cells to become more porous to entry of the foreign genes, some of which will be incorporated into the cell genome and express the gene products. In a culture containing $1\times10^6$ to $10^7$ cells, about one cell in a thousand actually incorporate the foreign DNA or genes, providing a sufficient concentration of the desired genes is present. Using a selectable marker aids identification and separation of cells incorporating the desired DNA for subsequent use.

Another aspect of the present invention is a process for providing animals with resistance to microbial infection or disease by introducing transformed animal cells of this invention into the animal. The transformed animal cells contain one or more genes coding for one or more antimicrobial agents selected from a cecropin, an attacin, a lysozyme, an S protein from lambda phage, an E protein from phage PhiX174, and a protein produced by gene 13 of phage 22. The means, procedures and processes for transforming animal cells are as described above. Further, the types of cells transformed are also described above. In general, the process is applicable to any animal subject to microbial infection or diseases with which the antimicrobial agents of this invention deal effectively. Typically, only domesticated animals of economic significance are of interest with regard to this process. However, for the prevention of contagious infection or disease, practically any animal is included within the scope of the invention. Practically, however, only those animals which are readily available for introduction of transformed cells, e.g., animals which are kept in confined areas or regularly gathered for inspection, treatment, marketing and the like, are more easily treated. Specifically, animals selected from cattle, horses, pigs, sheep, goats, dogs and cats are included in the animals amenable to the present process. Fowl such as ducks, geese, chickens, turkeys and the like are also included. Additionally, fish and other marine animals or aquaculturally produced species are included.

In one aspect of the invention, the process includes introducing into the animal transformed cells to provide cells which fight certain infections or disease states by expressing the antimicrobial agents. Methods for obtaining transformable cells from a live animal are known and conventional. These methods include surgical procedures, bone marrow collection and transfer, biopsies, and the like. The cells are then transformed according to the processes described herein and reintroduced to the animal using conventional surgical or other techniques mentioned above. The cells are not rejected because they are the animal's own cells, but the stress of the gathering, transformation or reintroduction may result in a significant number of nonviable transformed cells or problems with the host animal's implantation site. The process of this aspect of the invention can be used as a treatment process or alternatively as a prophylactic procedure for preventing disease or infection to exposed animals.

Although the previously described process of transformation of animal cells includes embryos, the present invention particularly includes preimplantation stage embryos, and in certain cases, but not preferably, implanted embryos, containing in their genomes one or more genes coding for one or more antimicrobial agents selected from the group consisting of cecropins, attacins, lysozymes, an S protein from lambda phage, an E protein from phage PhiX174 and a protein produced by gene 13 of phage 22. The embryos of particular interest to this feature of the invention are preimplantation stage embryos selected from, but not limited to, zygotes or one-cell embryos, 2-cell embryos, 4-cell embryos, 8-cell embryos, morulae and blastocysts, including hatched blastocysts. The transformation of such embryos with one or more genes coding for one or more antimicrobial agents of this invention is accomplished by processes described above, e.g., transfection of the embryos with retroviral vectors carrying one or more genes for the antimicrobial agents, electroporation of the embryos, treatment of the embryos with a chemical transformant solution containing one or more genes coding for said antimicrobial agents, and microinjection of the embryos with one or more genes coding for the antimicrobial agents. Microinjection is also a known and conventional procedure. However, it is highly specific and requires each embryo to be treated individually. In contrast, retroviral vector procedures treat a number of embryos at a time. The DNA transfection or chemical transformation procedures are useful, but require a greater number of embryos in order to be effective. Thus, microinjection, retroviral vectors or electroporation are preferred transformation processes for embryos because the success ratio is higher than for other processes and fewer embryos are required to accomplish a desired result. Of course, the feature of transforming embryos by the process of this invention is that the genes enter the embryonic genome and are replicated with the growing post-implant zygote which eventually results, after gestation and birth or incubation or culturing and hatching, in a transformed animal having one or more of the antimicrobial agents expressed in its genes and which can pass these characteristics onto its progeny. Thus, a further aspect and feature of the present invention is an animal having in its genome one or more genes coding for one or more antimicrobial agents selected from the group consisting of cecropins, attacins, lysozymes, an S protein from lambda phage, an E protein from phage PhiX174, and a protein produced from gene 13 of phage 22, such that the animal is resistant to microbial diseases affected by the antimicrobial agent, especially such agents as are included in the animal's genome.

Preferably, transformed animals are selected, as before, from cattle, horses, pigs, sheep, goats, dogs, cats, fowl, fish, and aquacultural species, although other animals including those raised for fur, hides, exhibition, entertainment and observation, or simply species preservation, can likewise become transformed animals according to this invention. Preferably, animals of economic importance are transformed and are included in this feature of the invention.

The transformed animals of the present invention are resistant to a number of disease- and infection-causing microorganisms, including bacteria, fungi and protozoa. Specifically, microbes selected from the general classes of Brucella, Listeria, Pseudomonas, Staphylococcus, Trypanosoma and Plasmodium are included in the group to which the transformed animals of the present invention are resistant. More specifically, the transformed animals are resistant to microorganisms selected from *Brucella abortus, Plasmodium falciparum, Trvoanosoma cruzi, Listeria monocytogenes, Pseudomonas aerugenosa, Staphylococcus aurens*, and the like. Each of the transformed animals has in its genome one or more genes which express one or more antimicrobial agents as described hereinabove for the specific genes coding for the antimicrobial agents.

In a still further aspect and feature of the present invention is a method of treatment for animals which are not transformed includes direct injection intramuscularly, intraperitoneally, subcutaneously or intravenously of one or more antimicrobial agents of this invention in an antimicrobially effective amount. Preferably, the antimicrobial agent in unit dosage form includes an acceptable pharmaceutical carrier. Typical examples include unit dosage forms which range in concentration from about 10 to about 150 milligrams of antimicrobial agent per kilogram of animal body weight, preferably from about 11 to about 110 mg per kg. Specifically, when cecropin is the antimicrobial agent, a unit dosage amount includes about 10 to about 150 milligrams of cecropin per kilogram of body weight for the animal, preferably from about 11 to about 110 mg per kg.

Specifically, the diseases against which such treatment effectively prevents or mitigates the severity of infection cr disease include those referred to hereinabove. A preferred method of treatment of animals for microbial infections or diseases comprises administering to such animals an antimicrobially effective amount, as defined hereinabove, of one or more antimicrobial agents selected from the group consisting of a cecropin, an attacin, a lysozyme, an S protein from lambda phage, an E protein from phage PhiX174, and a protein produced by gene 13 of phage 22. Typically and more preferably, the antimicrobial agent is a cecropin and is selected from Cecropin A, Cecropin B, Cecropin D, or the like. Most preferred of the cecropins is a modified cecropin having 37 amino acids with a methionine and proline added at the amino end and no internal methionines. The preferred amino acid sequences of typical useful polypeptide antimicrobial agents are given in Table 1 above.

Another feature of the present invention provides a medicinal composition which includes, in various formulations and with various pharmaceutical carriers, a unit dosage form of the antimicrobial agents of this invention which are selected from a cecropin, an attacin, a lysozyme, an S protein from lambda phage, an E protein from phage PhiX174, and a protein produced by gene 13 of phage 22. Acceptable pharmaceutical carriers include water, alcohol, solvents and oils in the form of aromatic waters, liquors, solutions, tinctures, elixirs, spirits, perenteral solutions, physiologically buffered media, and the like. The unit dosage form of medicinal composition can be used for treating, humans and animals, including those described above. Unit dosage forms have the same amount of antimicrobial agent as disclosed for the method of treatment or some fractional equivalent thereof to provide a treatment regimen employed over a period of time. The optimum upper and lower therapeutic amounts and any contra-indications have not yet been fully established.

The safety of antimicrobial agents according to the present invention was tested according to standard procedures in animal studies. The procedures and results are given in the following Example 1.

EXAMPLE 1

Part A

Six BALB/C mice, 4 to 5 weeks of age, maintained on commercial rodent ration fed ad libidum and in general good health were each inoculated with 1.76 milligrams/day of cecropin C-37 in balanced salt solution intramuscularly for 4 consecutive days. No other change was made in diet or conditions. The mice were observed twice daily and no adverse reactions were noted. At the end of the fourth day, three of the nine were humanely destroyed and examined. After 30 days, 3 of the 6 were given an additional 1.76 milligrams each. No adverse reactions were noted.

The remaining mice were all killed 7 days after the last inoculation. Examination of organs and tissues indicated no gross pathological changes were present in the organs or at the injection sites. None of these mice produced detectable levels of IgG antibody to the antimicrobial agent.

Part B

Following the procedure above in Part A, three BALB/C mice were given 110 milligrams/kilogram of body weight of cecropin C-37 injected intramuscularly in balanced salt solution for 6 days. White cell counts and differentials were performed on a daily basis. Ten days after the last inoculation, the mice were again injected intramuscularly with 110 milligrams/kilogram of body weight with Cecropin C-37. Observation revealed no adverse effects during the procedure. All three mice were killed 7 days after the final inoculation and tissues were examined. All mice had enlarged spleens but were otherwise unremarkable. No Cecropin C-37 antibodies were detected.

The method of treatment of an animal employing the antimicrobial agents of this invention are illustrated by the following Examples.

EXAMPLE 2

A total of 18 BALB/C mice, maintained on commercial rodent ration fed ad libidum, 4 to 5 weeks of age and in good health were inoculated intraperitoneally with 3 to $5 \times 10^8$ Brucella abortus in physiological saline. On the 12th day post infection, 6 of the mice were each inoculated intramuscularly with 0.176 milligrams/day of cecropin C-37 antimicrobial agent in balanced salts, 6 were likewise treated with 0.176 milligrams/day of tetracycline and 6 were likewise given sterile water, all for a period of 4 days. Then, nine mice were sacrificed on the 16th day post infection and spleen tissue examined morphologically, histologically and by culturing according to standard procedures for *Brucella abortus*. The concentrations found are given in the following table.

TABLE 2

Concentration of *Brucella abortus* in BALB/c Mouse Spleen Tissue After 4 Days Treatment (per gram of spleen)

| Control | Tetracycline | Cecropin C-37 |
|---|---|---|
| $8.15 \times 10^3$ | $4.4 \times 10^3$ | $1.59 \times 10^3$ |

The remaining 9 mice were sacrificed on the 23rd day post infection and examined in the same manner and no difference in result was observed. This result indicates that the antimicrobial agent of this invention is capable of significantly decreasing the level of infection and growth of *Brucella abortus* in mice.

In vitro evaluation of the antimicrobial agents of this invention were carried out by the following general procedure. A known number of viable microorganisms were exposed to a known concentration of the antimicrobial agent for a given time period. Following exposure, the undiluted or diluted microorganisms were plated on solid growth media, e.g., agar plates. The plates were incubated and numbers of organisms determined by making plate counts. Comparisons are then made with the non-treated bacteria for evidence of inhibition, mortality, or both. The following Examples give detailed experimental procedures and results for several microorganisms and antimicrobial agents.

EXAMPLE 3

To a suitable container was added 50 microliters of the bacteria under investigation, in this instance, *E. coli* E/2/64, obtained from Cornell University, and 50 microliters of phosphate buffered saline solution (PBS), prepared from NaCl–80.0 g, KCl–3 g, $Na_2HPO_4$–0.73 g, $KH_2PO_4$–0.2 g, with dilution of 10 milliliters of mixture with 90 milliliters of water and sterilize by autoclaving. The *E. coli* is collected in late log phase growth at which the majority of cells are in growth phase at 18–24 hours. In addition, the same mixture was prepared with 50 microliters of natural cecropin B or modified cecropin C-37. The mixtures were incubated at room temperature for 1 hour, and then at 37° C. for 30 minutes. The mixtures were diluted to $10^{-1}$ or $10^{-3}$ with serial dilutions at 7 drops per dilution (10 microliters per drop), plated on agar growth media, which is a tryptose agar. The plates were incubated for 3 days at 37° C. Plate counts were then made and the results given below.

TABLE 3

Effect of Antimicrobial Agent on *E. coli*

| Antimicrobial Agent | Concentration | Results |
|---|---|---|
| Cecropin B | $5 \times 10^{-6}$ molar | no growth |
| Cecropin C-37 | $5 \times 10^{-6}$ molar | no growth |

Combinations of both natural cecropin B and cecropin C-37 with lysozyme (25:25 microliter mixture) also prevented growth at $10^{31\ 7}$ molar concentrations, but lysozyme itself at concentrations of 10 micrograms, 1 milligram, and 10 milligrams per milliliter all showed positive growth of *E. coli* at both $10^{-1}$ and $10^{-3}$ dilutions. Further, lower concentrations of 1 nanomolar and 1 micromolar of both cecropin species showed positive *E. coli* growth.

EXAMPLE 4

The procedure of Example 3 was followed, except the microorganism was *Brucella abortus*, isolated by conventional procedure. The results are shown in Table 4 below.

TABLE 4

Effect of Antimicrobial Agent on *Brucella abortus*

| Antimicrobial Agent | Concentration | Results |
|---|---|---|
| Cecropin B | $5 \times 10^{-5}$ molar | no growth |
| Cecropin C-37 | $5 \times 10^{-5}$ molar | no growth |

Combinations of modified Cecropin C-37 and natural cecropin B with lysozyme at 10 micrograms, 1 milligram and 10 milligrams per milliliter were effective to prevent growth only at the lowest concentration of lysozyme with cecropin C-37; otherwise, some growth of the *B. abortus* was noted.

The effect of antimicrobial agents of the present invention on *Trycanosoma cruzi* was investigated and the results and procedure are given in the following Example(s).

EXAMPLE 5

When Vero cells were infected on a 1:1 ratio with Trypanosomes which had been treated by soaking in a 100 micromolar solution of Cecropin B modified (C-37) antimicrobial agent in balanced salt prior to the infection process, the Vero cells had no infection with Trypomastigotes compared to 15 percent infection with a non-treated controls sample. The cecropin C-37 was completely effective in destroying the pathogen.

The effect of the antimicrobial agents of this invention on the malarial agent *Plasmodium falciparum* is illustrated in the Example below. *Plasmodium falciparum* attacks human red blood cells and remains in them. Because the red cell has no DNA itself, when the *P. falciparum*-containing red blood cell is treated with tritiated hypoxanthine, the radioactively labeled compound will be taken up by the live malarial parasite's DNA. Thus, radiation counts from the labeled $H^3$ will indicate the degree to which the antimicrobial agent successfully destroys the microorganism, i.e., the higher the radiated counts, the more viable *P. falciparum* extant.

EXAMPLE 6

Monolayer culture of Vero cells, derived from African Green Monkey kidney cells and available commercially, are infected by trypomastigote stage of *Trypanosoma cruzi*. The number of infected cells are determined by counting the amastigotes which develop intracellularly following penetration by the parasites. The cells were grown in microscope slide chambers at a density of about 100,000 cells per cubic millimeter. After a period of exposure by *Trypanosoma cruzi* to the Vero cells at a 1:1 ratio, several of the chambers were treated with Cecropin C-37 at a concentration of 100 micromolar. The slide chambers were fixed with formalin at various periods, usually 48, 72 and 95 hours post-infection, and then stained with geimsa. Random counts were made along a line down the microscope slide until several hundred cells were counted in replicates per slide. The results in numbers of amastigotes infecting the cells over time are given in the Table below.

TABLE 5

Effect of Antimicrobial Agent on *Trypansoma cruzi*

| Hours Post-Infection | No. of Amastigotes per 100 Mammalian Cells | | Average No. of Amastigotes per Infected Cell | | % of Cells Infected w/ Amastigotes | |
|---|---|---|---|---|---|---|
| | Control | Treated | Control | Treated | Control | Treated |
| 48 | 20 | 15 | 3 | 3 | 15 | 14 |
| 72 | 50 | 5 | 4 | 3 | 16 | 2.5 |
| 96 | 225 | 0 | 17 | 1.5 | 14 | 0 |

EXAMPLE 7

To four 150 ml culture flasks containing 50 ml of human red blood cells was added 0.5 weight percent of *Plasmodium falciparum* microorganisms in RPMI media. The mixture was cultured for a week under the conditions of 37° C. and $CO_2$ incubator. Then, with one flask not having anything added ani serving as a control, varied amounts of a cecropin C-37 and $10^{-5}$ molar solution of hypoxanthine containing 50 microcuries of tritiated hypoxanthine in the same media solution was added. The concentrations of experiments carried out included 1 micromolar, 20 micromolar and 200 micromolar amounts of cecropin C-37. After 24 hours at culture conditions, the solution was filtered off. The filter cake was measured with a liquid scintillation counter to determine the amount of uptake by the DNA of *P. falciparum*. The results are shown in Table 6 below.

The experiments were repeated at lower levels of infection with *P. falciparum*, i.e., 0.25 weight percent, 0.125 weight percent and 0.0625 weight percent. The results are also shown in Table 6.

TABLE 6

Uptake of Tritiated Hypoxanthine by *Plasmodium falciparum*

| Concentration of Antimicrobial | Counts per Minute × $10^{-1}$ | | | |
|---|---|---|---|---|
| (micromoles) | 0 | 1 | 20 | 200 |
| For Cecropin C-37 Percent Infection | | | | |
| 0.5 | 2720 | 2350 | 1925 | 60 |
| 0.25 | 1200 | 1053 | 946 | 40 |
| 0.125 | 520 | 470 | 435 | 30 |
| 0.0625 | 340 | 315 | 295 | 20 |
| For Cecropin C-35 Percent Infection | | | | |
| 0.5 | 2730 | 2860 | 2333 | 50 |
| 0.25 | 1333 | 1293 | 1066 | 40 |
| 0.125 | 625 | 565 | 495 | 20 |
| 0.0625 | 395 | 380 | 405 | 25 |

The results shown in the Table above indicate that as the concentration of antimicrobial agent increases from 0 (the control) to 200 micromolar, the counts per minute decrease, in most instances even at low concentrations and dramatically at higher concentrations. The lower counts indicate that the pathogenic microorganism is not taking up the tritiated hypoxanthine and the reason for this is that the antimicrobial agent is having an adverse affect on the pathogenic microorganism.

The effect of the antimicrobial agents of this invention on yeast is illustrated in the following example.

EXAMPLE 8

The yeast *Saccharomyces cerevisiae* was grown to late log phase in nutrient broth containing 10 grams tryptose and 5 grams of yeast extract plus 2 weight percent glucose. It was then diluted to about 500,000 cells per milliliter in 0.01M phosphate buffer solution at pH 6.8. Then the appropriate antimicrobial agents, controls or previously known lysing agents were introduced at molar concentrations indicated in the Table below and the resultant solutions incubated at 37° C. for 1 hour. The solutions were diluted 1000 fold and plated on nutrient agar plus glucose. The next day, plate counts were taken and the level of surviving yeast determined. The results are given in the Table below. The control was an unrelated peptide of 15 amino acids synthesized in a manner similar to that used to produce cecropin 37. Mellitin is a natural cell lysing agent and was used to indicate the best condition.

TABLE 7

Effect of Antimicrobial Agents on Yeast (*Saccharomyces cerevisiae*)

| | Number of Yeast Cells After Treatment (× 1000) | | | |
|---|---|---|---|---|
| Antimicrobial Agent | Control | Mellitin | Cecropin | Cecropin 37 |
| Molar Concentration of Antimicrobial Agent | | | | |
| 0 | 500 | 500 | 500 | 500 |
| $5 \times 10^{-6}$ | 500 | 260 | 500 | 400 |
| $5 \times 10^{-5}$ | 500 | 0 | 75 | 75 |

TABLE 7-continued

Effect of Antimicrobial Agents on Yeast (*Saccharomyces cerevisiae*)

| | Number of Yeast Cells After Treatment (× 1000) | | | |
|---|---|---|---|---|
| Antimicrobial Agent | Control | Mellitin | Cecropin | Cecropin 37 |
| $7.5 \times 10^{-4}$ | 500 | — | 0 | 0 |

Although the antimicrobial agents of the present invention require a slightly higher concentration, they have an effect similar to a known lysing agent for yeast cells.

EXAMPLE 9

In a manner similar to Example 8 above, about 250,000 cells of *E. coli* was treated with each of the antimicrobial agents at various concentrations. The results are shown in Table 8 below.

TABLE 8

Effect of Antimicrobial Agents on *E. coli*

| Molar Concentration of Antimicrobial Agent | Control | Mellitin | Cecropin | Cecropin 37 |
|---|---|---|---|---|
| 0 | 260 | 260 | 260 | 260 |
| $6 \times 10^{-6}$ | 260 | 20 | 10 | 10 |
| $2.5 \times 10^{-4}$ | 333 | 10 | 10 | 10 |

EXAMPLE 10

In a manner similar to Example 8 above, several human and animal pathogenic bacteria were treated with an antimicrobial agent of this invention. The Pseudomonas and one of the Staphylococcus strains were antibiotic resistant strains. The results are given in the Table below.

TABLE 9

Treatment of Several Pathogenic Bacteria with Antimicrobial Agent

| | Number of Bacteria Cells After Treatment (× 1000) | | |
|---|---|---|---|
| Bacteria Type | Pseudomonas aerugenose | Staphylococcus intermedius | Staphylococcus intermedius (antibiotic) |
| Molar Concentration of Antimicrobial Agent | | | |
| 0 | 1000 | 1000 | 1000 |
| $1 \times 10^{-6}$ | 10 | 50 | 40 |
| $1 \times 10^{-5}$ | 0 | 20 | 20 |
| $1 \times 10^{-4}$ | 0 | 0 | 0 |

This result indicates the effectiveness of the antimicrobial agents of this invention in destroying human and animal pathogenic bacteria in vitro.

As indicated hereinabove, the antimicrobial agents of the present invention are incorporated into mammalian embryos by electroporation, microinjection or retroviral vectors. The following procedure can be used to transform mammalian embryos by electroporation.

Various stages of preimplantation embryos from one-cell to blastocyst stage are electroporated in a Biorad electroporator using voltage of 100 to 300 volts at pulse durations of 10 to 20 microseconds, pulse frequencies of 1, 2 or 3 and at temperatures of 4, 25 and 37° C. The embryos will be placed in either 0.35 molar sucrose solution or phosphate buffered saline (PBS) solution containing from 20 to 500 micrograms of DNA per milliliter encoding at least one antimicrobial agent described hereinabove, and preferably several, and then treated or shocked according to the above parameters. After treatment, the embryos are left undisturbed for 5 to 10 minutes and are then removed from the treating or shocking chamber, washed in fresh medium and are transferred and implanted or placed in synchronized recipient mammals for continued gestation and birth.

In a similar manner, mammalian or animal cells are electroporated, except that a greater number of cells are available, e.g., from about one hundred thousand to about one million cells can be placed in the treating chamber of the electroporator, and an increased pulse duration of 7 milliseconds or more at voltages from 100–400 volts. Additionally, if the foreign or antimicrobial gene is fused to a marker or selectable gene, such as a neomycin-resistance gene, after electroporation the treated cells can be cultured in a selection medium in which only transformed cells expressing the foreign gene will survive. Thus, insuring the transfer to an animal of active cells containing genes expressing one or more of the antimicrobial agents.

The microinjection process can be carried out by known techniques which are described for the antimicrobial agents of the present invention as follows. The transfer of genes coding for at least one antimicrobial agent of this invention are carried out on pronuclear stage embryos. Such pronuclear stage zygotes will be recovered 12 to 50 hours after breeding, depending on the species used including cattle, goats, pigs, sheep, mice and the like. The embryos will be collected and maintained on Dulbecco's phosphate buffered saline (PBS) supplemented with pyruvate, glucose, 10 weight percent heat-treated fetal calf serum and 1 weight percent antibiotic-antimycotic. Micromanipulations are performed using a Zeiss ICM 405 inverted microscope equipped with two Leitz micromanipulators. Two pico-liters of purified gene preparation for at least one of the antimicrobial agents are injected into the male (larger) pronuclei using a beveled glass micropipette having an outside diameter of 1–3 micrometers. Approximately 60 percent of the embryos survive the required manipulations and injection.

The embryos are immediately transferred to appropriate synchronized recipients following microinjection and subsequent pregnancies are carried to term.

The resulting offspring are evaluated for incorporation of the genes coding for the antimicrobial agents of this invention using a two-phase evaluation. DNA preparations from peripheral blood lymphocytes, skin and liver biopsies are tested for incorporation of the antimicrobial agent genes by Southern blots using a specific gene probe. In the second phase, animals testing positively by the Southern blot are challenged with various microbes to evaluate resistance. Generally, about 20 percent of microinjected offspring are transgenic.

The procedure for retroviral vector process is similar to that described by Van der Putten et al in Proceedings of the National Academy of Science of the U.S.A., Vol. 82, pages 6148–6152, September 1985, Cell Biology. According to that procedure, recombinant retroviral vector DNA was efficiently inserted into the mouse germ line via infection of preimplantation mouse embryos. The eight-cell stage embryos were flushed from oviduct-uterus junctions with modified Whittens medium, see Whitten, W. K., (1971) "Advances in Bioscience" $_6$, 129–139. The zona pelucida was removed using Pronase at 22 units/ml or acidified Tyrode's solution, see Nicholson, G. L. et al (1975), "Journal of Cell Biology", $_{66}$, 263–274. The embryos were cultured for 16 hours on top of monolayers of virus-producing cells in the presence of Polybrene (see Toyoshima et al, 1969, "Virology", 38, 414–436) at 4 micrograms per milliliter at 37° C. in Dulbecco's modified Eagle's medium plus 10 (v/v) percent fetal calf serum in 5 percent $CO_2$ in air. After infection, morulae were cultured about 2 to 4 hours in modified Whitten's medium under a layer of equilibrated paraffin oil (see Hoppe, P. et al, 1973, "Biological Reproduction", 8, 420–426) before transfer into hours of pseudopregnant females. Subsequent testing of the offspring, carried out as described above, evaluate the efficiency of transfer of the genes coding for antimicrobial agents of this invention.

More specifically, as used in the process of the present invention, the retroviral vector process for transformation of specific animals includes the incubation of a confluent monolayer of helper virus-free packaging cells producing retrovirus vector containing one or more genes coding for antimicrobial agents described above with embryonic or animal cells. The animal cells were previously cultured for 24 hours in Dulbecco's modified Eagle's medium with 10% fetal bovine serum containing Polybrene (DMEM-1) on the monolayer. After transduction, the cells were removed from the monolayer and cultured for an additional 12–36 hours, pelleted and resuspended in fresh medium. The cells were then transferred to host animals, usually by injection. Alternatively, the cells can be injected into various stage embryos. When using retroviral transfection for embryos or embryonic stem cells per se, a DMEM-1 medium containing virus particles is collected and microinjected into the perivitelline space of individual preimplantation embryos or the blastocoel in blastocyst stage embryos. After transduction, the embryos are transferred surgically to the synchronized recipient, according to conventional techniques.

Chemical transformation of embryonic animal cells according to this invention can be accomplished by calcium phosphate-mediated uptake using the procedure demonstrated by Wigler et al, supra, which is incorporated herein by reference as if fully set forth. This procedure is used in general to insert into the genome of mammalian cells growing in culture a fragment of DNA carrying one or more genes, in this instance, one or more genes coding for the antimicrobial agents described above.

Chemical transfection is carried out by pipetting a suspension of the DNA, including one or more genes coding for antimicrobial agents of this invention, completed into small precipitates with calcium phosphate, onto a monolayer of embryonic cells growing in a tissue culture dish. Efficiency of transfection can be increased by using diethylaminoethyl dextran or dextran sulfate instead of calcium phosphate or shocking the embryonic cells with glycerol after 2 hours of incubation. Under optimal conditions one embryonic cell in 100 to 1000 can be obtained which has integrated and expressed the antimicrobial genes. A selectable marker, included with the antimicrobial genes can be used to increase the usual $10^{-5}$ to $10^{-7}$ efficiency of chemical transfection using; for example, a mutant dihydrofolate reductase gene which protects the embryonic cells from methotrexate, provides a successful selector for embryonic cells incorporating the exogenous antimicrobial genes.

Advantageously, chemical transformation techniques are simple to perform, require no special equipment and involve no infectious agent, as in retroviral transfection; but multiple copies, usually in head to tail relation, are transferred and the efficiency for embryonic cells, which are numerically low, is lower.

One method of obtaining the antimicrobial agents of the present invention is illustratively described using cecropin as a model. However, the general procedure would be applicable to any of the antimicrobial agents useful in the present invention. The modified cecropin C-37 gene has been synthesized by a DNA synthesis machine as shown below:

GATCTATGCCGAAATGGAAAGTCTTCAA-GAAAATTGAAAAAGTCGGTCGCAACATTC GAAACGGTATTGTCAAGGCTGGACCAGC-GATCGCGGTTTTAGGCGAAGCCAAAGCGC TAGGATAA (SEQ ID NO:8)

ATACGGCTTTACCTTTCAGAAGTTCTTT-TAACTTTTTCAGCCAGCGTTGTAAG CTTTGC-CATAACAGTTCCGACCTG-GTCGCTAGCGCCAAAATCCGCTTCGGTTTCGCG ATCCTATTCTTAA (SEQ ID NO:9)

The above gene sequence was programmed into a DNA synthesizer commercially available from Applied Biosystems, and 6 DNA fragments were produced using the triester method as described by Ito et al, *Nucleic Acids Research*, Vol. 8, 5491 (1982). The fragments were treated with polynucleotide kinase to attach a phosphate group at the 5' end and heated for 5 minutes at 90° C. The treated fragments were mixed together in equimolar amounts in TE Buffer solution (0.01 molar Tris at pH 8 and 0.001 molar EDTA). The fragments were allowed to anneal slowly over 3 hours. Then the plasmid vector, which will allow insertion into a production site, in this instance, lambda left hand promoter plasmid, cut with BglII and EcoRI restriction enzymes, was added to the prepared fragments at 0.1 concentration based on the total DNA sequences originally employed. With the addition of T4 DNA ligase to the mixture of prepared gene sequences, the mixture was left overnight at 12.5° C. and the genes were incorporated into the plasmid vector.

To check the ligation of DNA sequences and insertion into the plasmid vector with appropriate expression of the desired polypeptide, competent cells of *E coli* HB101, obtained from Bethesda Research Laboratories, Bethesda, Md., as a frozen suspension at −70° C. with dry ice, were transformed by taking 100 microliters of the HB101, thawing on ice, in this presence of 10–100 nanograms of added DNA prepared in plasmid vector form above. The mixture is allowed to stand for 30 minutes, after which it is heat shocked by heating for 30 minutes at 42° C. Then, culture media to make up to 1 milliliter is added, about 900 microliters, and the mixture is allowed to sit for 2 hours at 37° C. Then, the mixture is divided and plated out on 10 plates and grown for 1 day. The plates are then examined and viable colonies picked and screened for the proper fragments by selecting clones growing in 1 ml of culture media, lysing with detergent, precipitating the plasmid, digesting with BglII and EcoRl restriction enzymes. Examination after agarose gel electrophoresis should show the plasmid and the cecropin gene upon agarose gel staining.

Once the proper clones are identified as properly sequenced, transformation into a suitable host and expression of the polypeptide useful as an antimicrobial agent can be accomplished. A polypeptide leader sequence, having the DNA polynucleotide sequence below, is fused to the cecropin gene:

GATCTATGAACTTCTCCCG-TATCTTTTTCTTCGTTTTCGCTCTGGT-TCTGGCTTCT ACTGTTTCCGCTGCACCGGAAC-CGG (SEQ ID NO:10)

ATACTTGAAGAGGGCATAGAAAAAGAAG-CAAAAGCGAGACCAAGACCGAAGA TGA-CAAAGGCGACGTGGCCTGGGCCCTAG (SEQ ID NO:11)

The fusion occurs by treating the above gene sequences with polynucleotide kinase in equimolar amounts in TE Buffer by heating at 90° C. and then cooling to 70° C., then equimolar amounts of pCEC1 (the cecropin gene in a plasmid vector) cut with BglII and the mixture is allowed to anneal slowly at room temperature. Then polynucleotide ligase is added in an amount sufficient to ligate the plasmid vector with pCEC1 overnight. The ligated plasmid, hereafter identified as pCEC2 (containing the plasmid vector, the cecropin leader sequence and the synthesized cecropin gene), is then transformed with *E. coli* HB101 in the same manner as indicated hereinabove. Appropriate clones are picked and separated, and identified as pCEC2. Then, pCEC2 is cut with BglII restriction enzyme, added to an equimolar amount of beta lactamase signal peptide also cut with BglII having the DNA sequence given below:

GATCTATGAGCATCCAGCACTTCCGTGT-TGCTCTGCCGTTCTTTGCTGCTTTCTGC-CTGCCG GGTTTTCGCTCACCCGGAG (SEQ ID NO:12)

ATACTCGTAGGTCGTGAAGGCACAAC-GAGACGGCAAGAAACGACGAAAGACG-GACGGC CCAAAAGCGAGTGGGCCTCCTAG (SEQ ID NO:13)

and, in the same manner as above, the above gene sequence is treated with polynucleotide kinase and then heated and annealed slowly at room temperature and ligating with T4 DNA ligase. The resulting solution contains a mixture in which a plasmid has the beta lactamase signal peptide sequence attached to a cecropin leader which is attached to the cecropin gene in at least some amount. This is determined by transforming again with *E. coli* HB101 culturing, picking suitable clones and cutting with BglII and EcoRl. The resulting mixture, which is pCEC2 which is BglII and EcoRl cut, is mixed with equimolar amounts of expression vector plasmid and pCEC2 plasmid ligated with polynucleotide ligase. The resulting plasmid mixture is transformed with *E. coli* HB101, suitable clones are selected and identified as having cecropin-secretary capability.

Having obtained *E. coli* with cecropin plasmid pCEC2 secreting properties, it is then necessary to scale up the process through a series of increasingly larger containers until thousand liter culture fermentor vessels are used and separate the desired cecropin or other antimicrobial polypeptide agent. An interim step of cyanogen bromide cleavage to obtain the active cecropin is envisioned by the process of the present invention.

Having described the present invention, one skilled in the art will readily envision changes and variations in the invention which are nevertheless within the spirit and scope thereof. Accordingly, it is desired that the present invention be limited only by the lawful scope of the following claims.

What is claim is:

1. A method of treating a non-insect animal infected with a fungus or a gram-negative bacteria, the method comprising administering to said animal a therapeutically effective amount of cecropin C-37.

2. The method of claim 1, wherein the cecropin C-37 is administered in vivo.

3. The method of claim 1, wherein the animal is a human.

4. The method of claim 1, wherein the cecropin C-37 is admninistered intramuscularly.

5. A pharmaceutical composition comprising an antibacterially effective amount of cecropin C-37 and a pharmaceutically acceptable carrier.

6. A method of inhibiting growth of a gram-negative bacteria or fungus in a non-insect animal comprising administering to said animal a therapeutically effective amount of cecropin C-37.

7. The method of claim 6, wherein said animal is a human.

8. The method of claim 6, wherein the cecropin C-37 is administered in vivo.

9. The method of claim 1, wherein the gram-negative bacteria is of a genus selected from the group consisting of Brucella, Escherichia and Pseudomonas.

10. The method of claim 1, wherein the gram-negative bacteria is *Brucella abortus*.

11. The method of claim 1, wherein the animal is a mammal.

12. The method of claim 6, wherein the cecropin is administered intramuscularly.

* * * * *